United States Patent
Goel

(10) Patent No.: US 9,688,613 B2
(45) Date of Patent: Jun. 27, 2017

(54) OMEGABALINS, GABA DERIVATIVES OF OMEGA-3 POLYUNSATURATED ACIDS, THEIR FORMULATIONS AND METHODS OF USE

(71) Applicant: Jiva Pharma, Inc., Ann Arbor, MI (US)

(72) Inventor: Om P Goel, Ann Arbor, MI (US)

(73) Assignee: Jiva Pharma, Inc., Ann Arbor, MI (US)

( * ) Notice: Subject to any disclaimer, the term of this patent is extended or adjusted under 35 U.S.C. 154(b) by 0 days.

(21) Appl. No.: 15/189,295

(22) Filed: Jun. 22, 2016

(65) Prior Publication Data

US 2016/0376223 A1    Dec. 29, 2016

Related U.S. Application Data

(60) Provisional application No. 62/183,813, filed on Jun. 24, 2015.

(51) Int. Cl.
  *C07C 229/30* (2006.01)
(52) U.S. Cl.
  CPC ................... *C07C 229/30* (2013.01)
(58) Field of Classification Search
  None
  See application file for complete search history.

(56) References Cited

U.S. PATENT DOCUMENTS 7,164,034 B2 * 1/2007 Dooley ............... A61K 31/00
                                                      554/103

OTHER PUBLICATIONS

Perumal Yogeeswari et al., An Update on GABA Analogs for CNS Drug Discovery, Recent Patents on CNS Drug Discovery, 2006, 1, 113-118.
Tomasz Plech et al., Studies on the anticonvulsant activity of 4-alkyl-1,2,4-triazole-3-thiones and their effect on GABAergic system, European Journal of Medicinal Chemistry 2014, 86, 690-699.
Kevin Burgess et al., Practical Asymmetric Syntheses of All Four 2,3-Methanoleucine Stereoisomers, Tetrahedron Letters, 1995, 36(16), 2725-2728.
Kevin Burgess et al., A γTurn Structure Induced by SMe 2S,3S 2,3-Methanomethonine, J. Am. Chem. Soc. 1994,116, 799-800.

* cited by examiner

*Primary Examiner* — Brian J Davis
(74) *Attorney, Agent, or Firm* — Technology Law PLLC; Karen L Kimble

(57) ABSTRACT

The present invention relates to omegabalins, which are GABA derivatives of omega-3 fatty acids, and their use in pharmaceutically-acceptable formulations for treating neuropathic pain, fibromyalgia, epilepsy, anxiety, depression, insomnia, Alzheimer's disease, and other neurological conditions.

12 Claims, 2 Drawing Sheets

OMEGABALINS, GABA DERIVATIVES OF OMEGA-3 POLYUNSATURATED ACIDS, THEIR FORMULATIONS AND METHODS OF USE

FIELD OF THE INVENTION

The present invention relates to "omegabalins" or γ-aminobutyric acid (GABA) derivatives in which omega-3 polyunsaturated acids are substituted for one hydrogen in γ-aminobutyric acid at its central 3-position carbon. These derivatives of omega-3 fatty acids are used in pharmaceutical formulations for treating neuropathic pain, fibromyalgia, epilepsy, anxiety, depression, Alzheimer's disease and other neurological conditions.

BACKGROUND OF THE INVENTION

γ-Amino butyric acid (GABA) is one of the major inhibitory neurotransmitters in the mammalian central nervous system. It plays the principal role in reducing neuronal excitability throughout the nervous system. GABA acts at inhibitory synapses in the brain by binding to specific transmembrane protein receptors in both pre- and post-synaptic neuronal processes. This binding causes the opening of ion channels to allow the flow of either negatively charged chloride ions into the cell or positively charged potassium ions out of the cell. This action results in stabilizing or causing hyperpolarization of the resting membrane potential. Two general classes of GABA receptor are known: 1) $GABA_A$ in which the ionotropic receptor is part of a ligand-gated ion channel complex, and 2) $GABA_B$ metabotropic receptors, which are G protein-coupled receptors that open or close ion channels via intermediaries (G proteins). (WIKI).

GABA does not cross the blood brain barrier (BBB) efficiently and brain cells make nearly all of the GABA found in the brain by decarboxylation of glutamic acid with pyridoxal phosphate. The deficiency of GABA in the brain is associated with a number of neurological disease states. When the concentration of GABA falls below a threshold level, then seizures occur, which are stopped by raising the brain GABA concentration. Other neurological conditions such as schizophrenia, Huntington's chorea, motion disorders, Alzheimer's disease, depression, and anxiety are linked to low levels of GABA and the enzyme glutamic acid decarboxylase (GAD), (e.g., K. Gaicy, et al., *Current Medicinal Chem.*, 2010, 17, 2338-2347; and numerous references cited therein).

Over the past half century or more, numerous GABA analogs with superior pharmacological properties have been synthesized, e.g., the classical discovery of baclofen; nipecotic acid, guvacine, and homo-β-proline. Commercially, gabapentin (cyclohexylgaba), and pregabalin (S-isobutyl-gaba) are hugely successful as add-on therapy for epilepsy, neuropathic pain, and fibromyalgia. All these compounds are lipophilic analogs of GABA, substituted at the central $3^{rd}$ carbon of GABA to facilitate diffusion across the BBB. (Perumal Yogeeswari, et al., *Recent Patents on CNS Drug Discovery*, 2006, 1, 113-118). Both gabapentin and pregabalin have an affinity for the L-amino acid transporter which facilitates transport across the BBB of zwitterionic endogenous amino acids such as leucine, isoleucine, and valine. This mechanism also provides support in the transport of exogenous γ-amino acids, gabapentin, pregabalin and numerous other synthetic analogs.

Recently, vigabatrin was approved to treat complex epilepsy in adults and children. Vigabatrin is unique in that it is a specific, irreversible inhibitor of the enzyme γ-aminobutyric acid α-oxoglutarate transaminase (GABA-T), which use leads to beneficial long lived elevated GABA levels in the brain. Vigabatrin, (RS)-4-aminohex-5-enoic acid, is an unusual analog of GABA, in that it has unsaturation, a vinyl group, in the 4-position of GABA. Most GABA analogs have saturated, short hydrocarbon chains attached at the central $3^{rd}$ carbon. The vinyl group in vigabatrin participates in the irreversible inhibition of the enzyme GABA-T, and sustains higher brain levels of GABA. (See WIKI for reaction mechanism). In contrast, recent discovery efforts have focused on conformationally constrained cyclopropyl β-amino acid analogs of pregabalin and gabapentin. These backbone-rigid analogs are expected to provide important modulation of different GABA receptors, (Burgess, K and Ho, K K, *J. Am. Chem Soc.*, 1994, 116, 799-800; Burgess, K. and Li, W, *Tetrahedron Lett.*, 1995, 16, 2725-2728).

Omega-3 oils or omega-3 fatty acids are naturally occurring, straight-chain (16-24 carbons) fatty carboxylic acids (PUFAs), essential for normal metabolism in humans and other animals. Since the omega-3 fatty acids are not synthesized by the human body, they are recommended to be taken as dietary supplements in 1-4 grams daily for cardiovascular health benefits, preventing strokes, and reducing blood pressure. (Delgado-Lista, J., et al., *The British Journal of Nutrition*, June 2012, 107 Suppl 2, S201-13).

Omega-3 fatty acids have 3-6 conjugated carbon-carbon double bonds and are so named as the first carbon with unsaturation is $3^{rd}$ carbon from the distal carboxylic acid carbon. All double bonds are in the cis configuration. Among the omega-3 fatty acids eicosapentanenoic acid (EPA, 20 carbons, 5 conjugated double bonds), docohexaenoic acid (DHA, 22 carbons, 6 conjugated double bonds) and α-linolenic acid (ALA, 18 carbons, 3 conjugated double bonds) are the most studied pharmacologically. The presence of omega-3 fatty acids, especially DHA in the brain is ubiquitous. Clinical studies in 4 year old children support the beneficial effects of docosohexaenoic acid (DHA) on cognitive function (NCT 00351624; 2006-2008; sponsored by Martek BioSciences Corporation). It would be an interesting study to follow such treated children over decades regarding the incidence of onset of symptoms of Alzheimer's disease relative to the untreated group.

Clearly, finding a GABA derivative that has the desired properties of crossing the BBB and provides the desired effects for treatment of neurological conditions is still needed.

BRIEF SUMMARY OF THE INVENTION

Omega-3 acids as used in the present invention offer an unexplored and unusual structural motif of lipophilic, long aliphatic carbon straight-chains, rich with 4-6 conjugated, all cis double bonds of 8-12 π electrons, which are bonded to GABA to form unique derivatives. As such, 3-substituted GABA derivatives of omega-3 acids in the present invention are previously unknown; and expected to have superior BBB crossing ability than their simpler analogs, such as pregabalin, and have possible longer lived biological response. It is also possible that one or more conjugated double bonds in omega-3 oils may participate in irreversible inhibition of the enzyme γ-amino butyric acid α-oxoglutarate transaminase (GABA-T) to increase GABA brain levels. Thus multiple beneficial modes of action are anticipated with the 3-GABA derivatives of omega-3 fatty acids. Some treatments using the pharmaceutically-acceptable formulations of Formula (I) compounds are for neuropathic pain, fibromyalgia, epilepsy, anxiety, depression, insomnia, Alzheimer's disease, and other neurological conditions.

These modified PUFA derivatives of GABA in the present invention are formed by reduction of the carboxylic acid of the omega-3s to an end methylene moiety with a leaving group X, such as a halide, mesylate or tosylate, which is displaced by a pre-gaba synthetic moiety. The following structure depicts these present compounds of Formula (I):

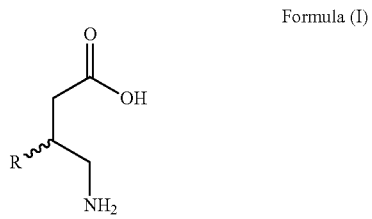

Formula (I)

wherein:

R is joined from the methylene moiety formed by reduction of the carboxylic acid of one of the following polyunsaturated fatty acids (PUFAs):
cis,cis,cis-7,10,13-hexadecatrienoic acid (HTA),
cis,cis,cis-9,12,15-octadecatrienoic acid (ALA),
cis,cis,cis-6,9,12,15-octadecatetraenoic acid (SDA),
cis,cis,cis-11,14,17-eicosatrienoic acid (ETE),
cis,cis,cis-8,11,14,17-eicosatetraenoic acid (ETA);
cis,cis,cis,cis-5,8,11,14,17-eicosapentanenoic acid (EPA),
cis,cis,cis,cis-6,9,12,15,18-heneicosapentaenoic acid (HPA),
cis,cis,cis,cis,cis-7,10,13,16,19-docosapentaenoic acid (DPA),
cis,cis,cis,cis,cis-4,7,10,13,16,19-docosahexaenoic acid (DHA),
cis,cis,cis,cis,cis-9,12,15,18,21-tetracosapentaeonic acid (TPA) or
cis,cis,cis,cis,cis-6,9,12,15,18,21-tetracosahexaeonic acid (THA); and
the wavy bond depicts the creation of a new chiral carbon center forming two enantiomers of R and S configuration and mixtures thereof. Thus two enantiomers of R and S configuration result from this joining of the PUFAs with the GABA moiety.

DETAILED DESCRIPTION OF THE INVENTION

Figure 1:
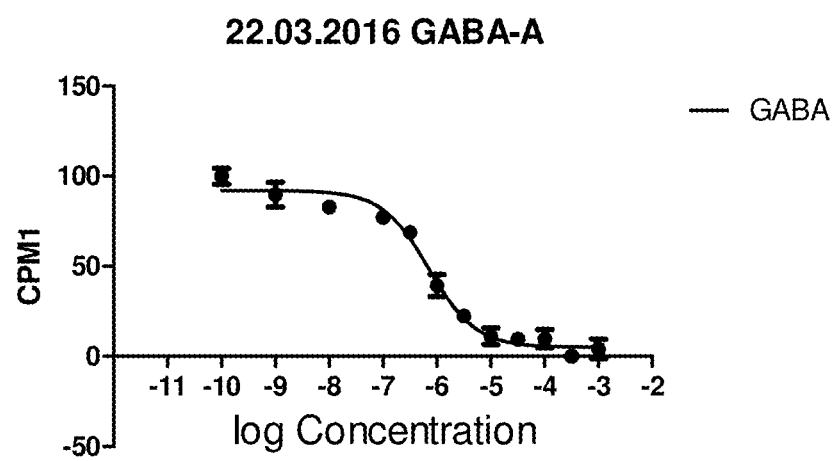
FIG. 1 graphically shows the affinity of GABA (γ-aminobutyric acid for GABA-A receptors labeled with [$^3$H] muscimol.

It is understood that the terminology used herein is for the purpose of describing particular embodiments only and is not intended to be limiting. As used in this specification, the singular forms "a", "an", and "the" include plural referents unless the content clearly indicates otherwise. The following terms in the Glossary as used in this application are to be defined as stated below and for these terms, the singular includes the plural.

Various headings are present to aid the reader, but are not the exclusive location of all aspects of that referenced subject matter and are not to be construed as limiting the location of such discussion.

Also, certain US patents and PCT published applications have been incorporated by reference. However, the text of such patents is only incorporated by reference to the extent that no conflict exists between such text and other statements set forth herein. In the event of such conflict, then any such conflicting text in such incorporated by reference US patent or PCT application is specifically not so incorporated in this patent.

Glossary

ALA means α-linolenic acid or cis,cis,cis-9,12,15-octadecatrienoic acid, having 18 carbons, 3 cis double bonds, that is modified by reduction of the carboxylic acid to a methylene moiety to be R of Formula (I), R,S-3-(amino methyl)-3-(14Z,17Z,20Z)-heneeicosanoic acid, and R shown by the formula below:

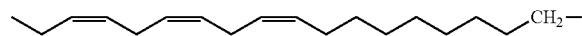

DHA means cis,cis,cis,cis,cis,cis-4,7,10,13,16,19-docosahexaenoic acid or docosahexaenoic acid, having 22 carbons, 6 cis double bonds, that is modified by reduction of the carboxylic acid to a methylene moiety to be R of Formula (I), R,S-3-(amino methyl)-3-(9Z,12Z,15Z,18Z,21Z,24Z)heptacosanoic acid, and R as shown by the formula below:

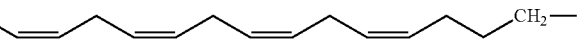

DPA means cis,cis,cis,cis,cis-7,10,13,16,19-docosapentaenoic acid or docosapentaenoic acid, having 22 carbons, 5 cis double bonds, that is modified by reduction of the carboxylic acid to a methylene moiety to be R of Formula (I), R,S-3-(amino methyl)-3-(12Z,15Z,18Z,21Z,24Z)tetracosanoic acid, and R as shown by the formula below:

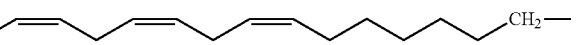

EPA means cis,cis,cis,cis-5,8,11,14,17-eicosapentanenoic acid or eicosapentaenoic acid, having 20 carbons, 5 cis double bonds, that is modified by reduction of the carboxylic acid to a methylene moiety to be R of Formula (I), R,S-3-(amino methyl)-3-(10Z,13Z,16Z,19Z, 22Z)-tricosanoic acid, and R as shown by the formula below:

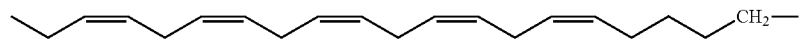

ETA means cis,cis,cis,cis-8,11,14,17-eicosatetranoic acid or eicosatetraenoic acid, having 20 carbons, 4 cis double bonds, that is modified by reduction of the carboxylic acid to a methylene moiety to be R of Formula (I), R,S-3-(amino methyl)-3-(13Z,16Z,19Z,22Z)-tricosanoic acid, and R as shown by the formula below:

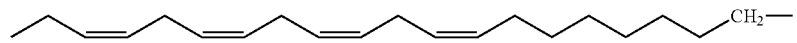

ETE means cis,cis,cis-11,14,17-eicosatrienoic acid or eicosatrienoic acid, having 20 carbons, 3 cis double bonds, that is modified by reduction of the carboxylic acid to a methylene moiety to be R of Formula (I), R,S-3-(amino methyl)-3-(16Z,19Z,22Z)-tricosanoic acid, and R as shown by the formula below:

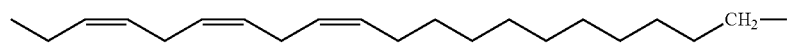

HPA means cis,cis,cis,cis,cis-6,9,12,15,18-heneicosapentaenoic acid or heneicosapentaenoic acid, having 21 carbons, 5 cis double bonds, that is modified by reduction of the carboxylic acid to a methylene moiety to be R of Formula (I), R,S-3-(amino methyl)-3-(11Z,14Z,17Z,20Z,23Z)-tetracosanoic acid, and R as shown by the formula below:

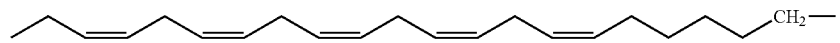

HTA means cis,cis,cis-7,10,13-hexadecatrienoic acid, having 16 carbons, 3 cis double bonds, that is modified by reduction of the carboxylic acid to a methylene moiety to be R of Formula (I), R,S-3-(amino methyl)-3-(12Z,15Z, 18Z)-nonadecanoic acid, and R as shown by the formula below:

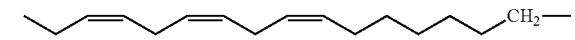

SDA means cis,cis,cis,cis-6,9,12,15-octadecatetraenoic acid or stearidonic acid, having 18 carbons, 4 cis double bonds, that is modified by reduction of the carboxylic acid to a methylene moiety to be R of Formula (I), R,S-3-(amino methyl)-3-(11Z,14Z,17Z,20Z)-heneicosanoic acid, and R as shown by the formula below:

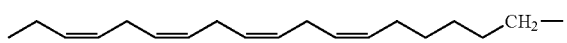

THA means cis,cis,cis,cis,cis,cis-6,9,12,15,18,21-tetracosahexaenoic acid, having 24 carbons, 6 cis double bonds, that is modified by reduction of the carboxylic acid to a methylene moiety to be R of Formula (I), R,S-3-(amino methyl)-3-(11Z,14Z,17Z,20Z,23Z,26Z)-heptacosanoic acid, and R as shown by the formula below:

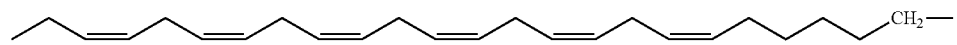

TPA means cis,cis,cis,cis,cis-9,12,15,18,21-tetracosapentaenoic acid, having 24 carbons, 5 cis double bonds, that is modified by reduction of the carboxylic acid to a methylene moiety to be R of Formula (I), R,S-3-(aminomethyl)-3-(14Z,17Z,20Z,23Z,27Z)-heptacosanoic acid, and R as shown by the formula below:

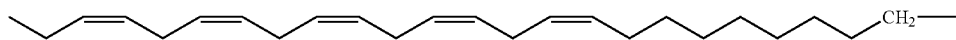

Omega-3 fatty acids means naturally occurring, straight-chain $C_{16}$-$C_{24}$ fatty carboxylic acids
BBB means blood brain barrier
Dess Martin reagent means 1,1,1-Triacetoxy-1,1-dihydro-1,2-benziodoxol-3(1H)-one
GABA means gamma amino butyric acid
PUFA means polyunsaturated fatty acids that are either naturally occurring omega-3 fatty acids or derivatives thereof
DIBALH means diisobutylaluminumhydride
LAH means lithium aluminum hydride
RT means room temperature or ambient temperature or about 22 to about 25° C.
rt means retention time in the context of determining purity by high performance liquid chromatography
TFA means trifluoroacetic acid
THF means tetrahydrofuran
w/w means weight by weight The present invention provides GABA compounds of Formula (I) that are derived from polyunsaturated omega-3 fatty acids (PUFAs) as defined in the Glossary as anticonvulsant, agents of the formula

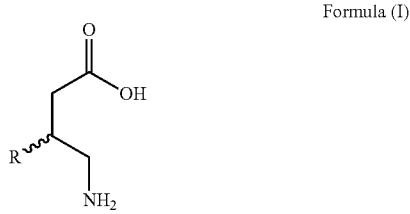

Formula (I)

wherein:
R is joined from the methylene moiety formed by reduction of the carboxylic acid of one of the following polyunsaturated fatty acids (PUFAs):
cis,cis,cis-7,10,13-hexadecatrienoic acid (HTA),
cis,cis,cis-9,12,15-octadecatrienoic acid (ALA),
cis,cis,cis,cis-6,9,12,15-octadecatetraenoic acid (SDA),
cis,cis,cis-11,14,17-eicosatrienoic acid (ETE),
cis,cis,cis,cis-8,11,14,17-eicosatetraenoic acid (ETA);
cis,cis,cis,cis,cis-5,8,11,14,17-eicosapentanenoic acid (EPA),
cis,cis,cis,cis,cis-6,9,12,15,18-heneicosapentaenoic acid (HPA),
cis,cis,cis,cis,cis-7,10,13,16,19-docosapentaenoic acid (DPA),
cis,cis,cis,cis,cis-4,7,10,13,16,19-docosahexaenoic acid (DHA),
cis,cis,cis,cis,cis-9,12,15,18,21-tetracosapentaenoic acid (TPA) or
cis,cis,cis,cis,cis-6,9,12,15,18,21-tetracosahexaenoic acid (THA); and the wavy bond depicts the creation of a new chiral carbon center.

Thus two enantiomers of R and S configuration result from this joining of the PUFAs with the GABA moiety as pure enantiomers as well as mixtures thereof.

It is anticipated that the S-stereoisomer or enantiomer will have much greater biological activity than the corresponding R-isomer.

The present invention utilizes the formation of compounds by modifying the carboxylic acid of the PUFA and covalently joining a GABA functionality, and tests if these compounds have "souped-up" GABA agonist activity and longer lived GABA levels in the brain for benefits in the treatment of neuropathic pain, fibromyalgia, epilepsy, anxiety, depression, insomnia, Alzheimer's disease, and/or other unique biological properties. Such compounds of Formula (I) can be used alone as a pharmaceutically-acceptable formulation, having pharmaceutically-acceptable salts, adjuvants, binders, desiccants, diluents and excipients. The formulation can be in the form of a solution for injection, ampoule, hard or soft gelatin capsule, tablet, or as a sustained release formulation.

Omega-3 acids offer an unexplored and unusual structural motif of long aliphatic carbon straight-chains rich with 4-6 conjugated, all cis double bonds of 8-12π electrons. As such, 3-substituted GABA derivatives of omega-3 acids are expected to have superior BBB crossing ability than their simpler analogs, such as pregabalin, and possible longer biological response. It is also possible that one or more conjugated double bonds in omega-3 oils may participate in irreversible inhibition of the enzyme γ-amino butyric acid α-oxoglutarate transaminase (GABA-T) to increase GABA brain levels. Thus multiple beneficial modes of action are anticipated with the 3-GABA derivatives of omega-3 fatty acids.

Alzheimer' Disease (AD)

The prevalence and incidence of Alzheimer's disease, and its devastating effects on the lives of patients and care giver families are well known. The health care costs to society are onerous, and will continue to grow with the aging population. Enormous strides have been made in understanding the pathology of the disease which leads to the build-up of amyloid plaques in the brain, which are aggregates of amyloid beta (Aβ) peptides. Fundamental advances have been made in discovering inhibitors of the extra-cellular and intra-cellular neuronal biochemical enzymes such as β-secretase (BACE1) or γ-secretase (GS) to stop the amyloid or intraneuronal τ-tangles build-up; and even reverse these processes through treatment with specific monoclonal antibodies. However, in spite of massive scientific research and investments in reversing the cognitive decline of AD, these have yielded scant benefits. Consensus is emerging that the best approach would be to treat patients before the disease has progressed too far, and even before disease symptoms become apparent. Multi-targeted Alzheimer's drugs, for example dual BACE/acetylcholine esterase inhibition or GSM/PPARγ active agents would offer additional benefits (Harrie J. M. Gisjen, et al., *Annual Reports in Medicinal Chemistry*, 2012, 47, 55-69).

The presence of omega-3 fatty acids, especially DHA in the brain is ubiquitous. Clinical studies in 4 year old children support the beneficial effects of docosohexaenoic acid (DHA) on cognitive function (NCT 00351624; 2006-2008; sponsored by Martek BioSciences Corporation). It would be an interesting study to follow such treated children over decades regarding the incidence of onset of symptoms of Alzheimer's disease relative to the untreated group. In the meantime, it is worth exploring in a prospective study, if the DHA-GABA conjugated derivative, either alone or in combination with a gamma secretase modulator (GSM) or other prescribed clinical agents, would slow down the decline of cognitive function in early stage AD patients.

This invention will be further clarified by a consideration of the following examples of synthesis of compounds of Formula (I) which are intended to be exemplary of the present invention.

General Synthesis Overview:

The DHA, EPA, and ALA analogs of isobutylgaba were prepared in 4 steps from their corresponding aldehyde. The aldehydes were prepared from the respective omega-3 ethyl ester, by partial reduction with DIBALH, THF, −78° C. or LAH followed by oxidation with the Dess Martin reagent.

The aldehydes were olefinated with commercially available t-butyl diethylphonoacetate 2 in good yields (70-80%). The nitromethyl group was added by Michael addition of nitromethane in the presence of base (tetramethylguanidine) in good yield (60-80% yield). However the reaction times were long (2-4 days). The nitro group was reduced with zinc in the presence of formic acid and the t-butyl ester was removed with TFA in dichloromethane. The products were then neutralized and purified by reverse phase chromatography. The final purification was generally run two times, which led to low recoveries of the final free amino acid (30-50%).

This synthesis sequence is shown by the general Scheme 1 below.

This general process scheme is shown in greater detail in the following examples.

EXAMPLE 1

Synthesis of a DHA Analog of Isobutylgaba (JIVA0039):
3-Aminomethyl-tetracosa-6,9,12,15,18,21-hexaenoic Acid Step 1). DHA olefin: tetracosa-2,6,9,12,15,18,21-heptaenoic acid tert-butyl ester

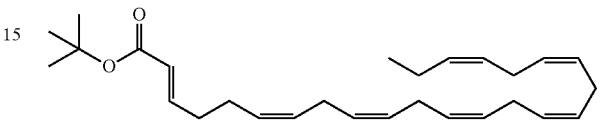

Sodium hydride (60%, 0.90 g, 22 mmol) was stirred with anhydrous THF (80 mL) under an argon atmosphere. The flask was cooled in an ice bath, tert-butyl diethylphosphonoacetate (6.5 g, 25 mmol) was added drop-wise over 20 minutes and the mixtures stirred for an additional 30 minutes before the DHA-aldehyde (6.3 g, 20 mmol) in THF (10 mL) was added. The ice bath was removed and the reaction stirred for 3-4 hours at RT. Water (100 mL) was added and the product was extracted with heptanes (2×50 mL). The combined heptanes extracts were dried over sodium sulfate, filtered, and concentrated. The crude oil (9.4 g) was purified by flash column chromatography on silica gel (200 g), eluting with 5% ethyl acetate in heptanes. The experiment produced tetracosa-2,6,9,12,15,18,21-heptaenoic acid tert-butyl ester (7.20 g, 75% yield) as a colorless oil, and is further characterized by:

$^1$H NMR (300 MHz, CDCl$_3$/TMS): δ 6.82 (dt, 1H, J=15.6, 6.6 Hz), 5.79 (d, 1H, J=15.6 Hz), 5.38 (m, 12 H), 2.83 (m, 10 H), 2.25 (m, 4H), 2.07 (m, 2H), 1.42 (s, 9H), 0.98 (t, 3H, J=7.7 Hz).

Scheme 1:

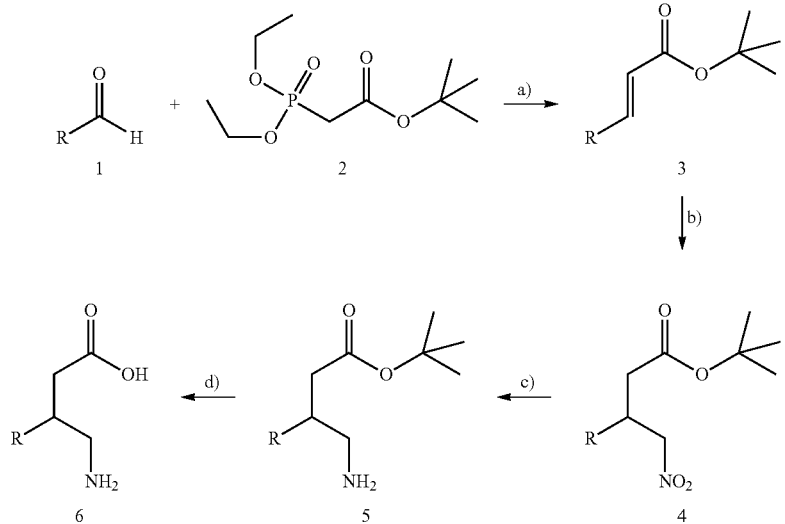

R = DHA, EPA, ALA
a) NaH, THF, RT, 4 hours; b) nitromethane, tetramethyl guanidine, RT, 2-4 days;
c) Zn, formic acid, RT, 1 hour; d) TFA Step 2). DHA-nitromethyl analog: 3-nitromethyl-tetracosa-6,9,12,15,18,21-hexaenoic acid tert-butyl ester

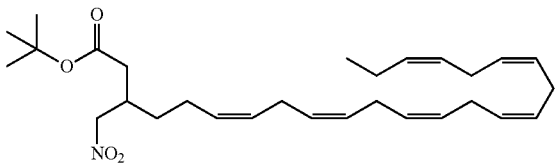 [SMILES: CC/C=C\C/C=C\C/C=C\C/C=C\C/C=C\C/C=C\CCC(CC(=O)OC(C)(C)C)C[N+](=O)[O-]]

To a solution of tetracosa-2,6,9,12,15,18,21-heptaenoic acid tert-butyl ester (7.20 g, 18.8 mmol) in nitromethane (80 mL) was added 1,1,3,3-tetramethylguanidine (3.0 g, 26 mmol). The resulting reaction mixture was allowed to stir at RT for 2 days. After 2 days, ethyl acetate (100 mL) was added and the base was extracted with 5% hydrochloroic acid solution (100 mL). The ethyl acetate extract was dried over sodium sulfate, filtered and concentrated. The crude oil (7.93 g) was purified by silica gel column chromatography (5% to 15% ethyl acetate/heptane) that provided 3-nitromethyl-tetracosa-6,9,12,15,18,21-hexaenoic acid tert-butyl ester as colorless oil (5.11 g, 57.6% yield), and is further characterized by:

$^1$H NMR (300 MHz, CDCl$_3$/TMS): δ 5.38 (m, 12 H), 4.47 (m, 2H), 2.83 (m, 10 H), 2.60 (m, 1H), 2.35 (m, 2H), 2.16-2.05 (m, 2H), 1.45 (s, 9H), 0.98 (t, 3H, J=7.7 Hz).

Steps 3,4): DHA analog of isobutylgaba (JIVA0039): 3-Aminomethyl-tetracosa-6,9,12,15,18,21-hexaenoic acid

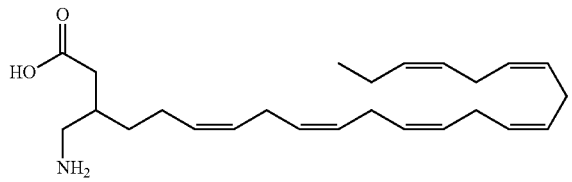 [SMILES: CC/C=C\C/C=C\C/C=C\C/C=C\C/C=C\C/C=C\CCC(CN)CC(=O)O]

Zinc dust (2.50 g) was stirred with 5% hydrochloric acid (50 mL) for 4 to 5 minutes, filtered, and washed with DI water (50 mL) and methanol (50 mL). The activated zinc was added to methanol (60 mL) containing formic acid (3 mL, 97%) and 3-nitromethyl-tetracosa-6,9,12,15,18,21-hexaenoic acid tert-butyl ester (2.50 g, 5.3 mmol). The mixture stirred for 2 hours at RT (flask was kept in a water bath to maintain RT). Toluene (60 mL) was added and the mixture was filtered through a pad of celite to remove the zinc. The methanol/toluene was concentrated on a rotovap. The remaining oil was dissolved in dichloromethane (50 mL) and filtered to remove traces of zinc. The dichloromethane solution was added TFA (7.0 mL) and the solution stirred at RT under an argon atmosphere for 24 hours. After 24 hours, the solution was concentrated on a rotovap at RT. Toluene (25 mL) was added and the solution was concentrated again to remove TFA. The remaining oil was partitioned between water (25 mL) and dichloromethane (50 mL) and concentrated ammonium hydroxide solution (2-3 mL) was added until the aqueous fraction was neutral. The dichloromethane layer was separated and the aqueous portion was extracted with dichloromethane (25 mL). The combined dichloromethane extracts were dried over sodium sulfate, filtered, and concentrated. The reaction generated 2.0 g of crude free base that was a brown gel. The experiment was repeated a second time on the same scale and under the same conditions to generate a second 2 g batch of the DHA-isobutylgaba analog. The material from both batches was combined and purified on a C18 reverse phase column (50 g, 17% carbon load) using a linear gradient of methanol/DI water (30% methanol to 100%) methanol. The purification was repeated 3 times in order to prepare 3-aminomethyl-tetracosa-6,9,12,15,18,21-hexaenoic acid (JIVA0039) (1.2 g, 30% yield) as a light yellow gel, and is further characterized by:

Analysis:

Appearance: light yellow gel

Chemical Formula: $C_{25}H_{39}NO_2$

Molecular Weight: 385.58

Chromatographic purity (HPLC): 94.8% (rt=13.152 min, 73-100% MeOH/H2O+0.1% TFA) over 10 min., hold 10 min., Altima C-18, 5μ, 4.6×250 mm, 1.0 mL/min, 5 μL injection, 40° C., UV detection, 210 nm)

HRMS (ESI): Calculated for $C_{25}H_{40}NO_2$ $(M+H)^+$: 386.3054, found 386.3062.

$^1$H NMR (300 MHz, CD$_3$OD/TMS): δ 5.36 (m, 12 H), 2.99 (dd, 1 H, J=15.5, 3.6 Hz), 2.85-2.70 (m, 11 H), 2.47 (dd, 1H, J=15.9, 3.6), 2.30 (dd, 1H, J=15.9,8.6 Hz), 2.19-2.00 (m, 5H), 1.44 (m, 2H), 0.97(t, 3H, J=7.5 Hz).

$^{13}$C NMR (300 MHz, CD$_3$OD/TMS): δ 180.5, 132.9, 129.8, 129.6, 129.3, 129.2, 129.0, 128.3, 45.6, 42.9, 35.2, 33.9, 26.7, 26.5, 25.6, 21.6, 14.8.

EXAMPLE 2

Synthesis of EPA Analog of Isobutylgaba (JIVA0040):
3-Aminomethyl-docosa-7,10,13,16,19-pentaenoic Acid Step 1): EPA-olefin: Docosa-2,7,10,13,16,19-hexaenoic acid tert-butyl ester

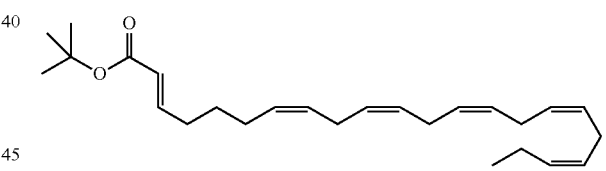

Sodium hydride (60%, 0.70 g, 17.5 mmol) was stirred with anhydrous THF (75 mL) under an argon atmosphere. The flask was cooled in an ice bath, tert-butyl diethylphosphonoacetate (5.0 g, 19.8 mmol) was added drop-wise over 20 minutes and the mixture stirred for an additional 30 minutes before the EPA-aldehyde (4.0 g, 14 mmol) in THF (10 mL) was added. The ice bath was removed and the reaction stirred for 3-4 hours at RT. Water (100 mL) was added and the product was extracted with heptanes (2×50 mL). The combined heptanes extracts were dried over sodium sulfate, filtered, and concentrated. The crude oil (6.7 g) was purified by flash column chromatography on silica gel (140 g), eluting with 2%-5% ethyl acetate in heptanes. The experiment produced docosa-2,7,10,13,16,19-hexaenoic acid tert-butyl ester (4.44 g, 83% yield) as a colorless oil, and is further characterized by:

$^1$H NMR (300 MHz, CDCl$_3$/TMS): δ 6.88 (dt, 1H, J=15.6, 6.6 Hz), 5.75 (d, 1H, J=15.6 Hz), 5.39 (m, 10 H), 2.84 (m, 8 H), 2.24-2.05 (m, 6H), 1.50 (s, 9H), 0.99 (t, 3H, J=7.7 Hz).

Step 2): EPA-nitromethyl analog: 3-Nitromethyl-docosa-7,10,13,16,19-pentaenoic acid tert-butyl ester.

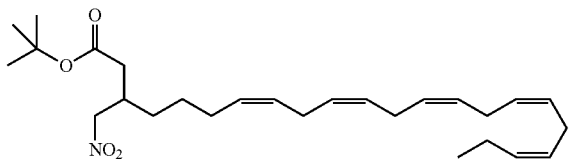 [SMILES: CC/C=C\C/C=C\C/C=C\C/C=C\C/C=C\CCCC(CC(=O)OC(C)(C)C)C[N+](=O)[O-]]

To a solution of docosa-2,7,10,13,16,19-hexaenoic acid tert-butyl ester (4.40, 18.8 mmol) in nitromethane (40 mL) was added 1,1,3,3-tetramethylguanidine (2.0 g, 17.2 mmol). The resulting reaction mixture was allowed to stir at RT for 3 days. After 3 days, ethyl acetate (100 mL) was added and the base was extracted with 5% hydrochloric acid solution (100 mL). The ethyl acetate extract was dried over sodium sulfate, filtered and concentrated. The crude oil (5.05 g) was purified by silica gel (180 g) column chromatography (5% ethyl acetate/heptane). The experiment provided 3-nitromethyl-docosa-7,10,13,16,19-pentaenoic acid tert-butyl ester (4.0 g, 80% yield), as a colorless oil, and is further characterized by:

$^1$H NMR (300 MHz, CDCl$_3$/TMS): δ 5.38 (m, 12 H), 4.47 (m, 2H), 2.83 (m, 10 H), 2.60 (m, 1H), 2.35 (m, 2H), 2.16-2.05 (m, 2H), 1.45 (s, 9H), 0.98 (t, 3H, J=7.7 Hz).

Steps 3,4). EPA-isobutylgaba analog (JIVA 0040): 3-Aminomethyl-docosa-7,10,13,16,19-pentaenoic acid

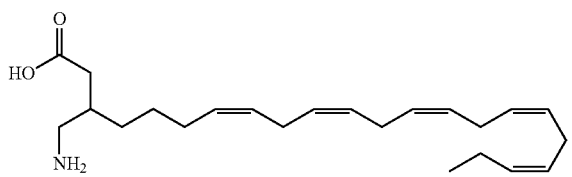 [SMILES: CC/C=C\C/C=C\C/C=C\C/C=C\C/C=C\CCCC(CN)CC(=O)O]

Zinc dust (4.0 g) was stirred with 5% hydrochloric acid (40 mL) for 4 to 5 minutes, filtered, and washed with DI water (80 mL) and methanol (80 mL). The activated zinc was added to methanol (80 mL) containing formic acid (4 mL, 97%) and 3-nitromethyl-docosa-7,10,13,16,19-pentaenoic acid tert-butyl ester (4.0 g, 8.97 mmol). The mixture stirred for 2 hours at RT (flask was kept in a water bath to maintain RT). Toluene (80 mL) was added and the mixture was filtered through a pad of celite to remove the zinc. The methanol/toluene was concentrated on a rotovap. The remaining oil (4.7 g) was dissolved in dichloromethane (60 mL) and filtered to remove traces of zinc. The dichloromethane solution was added TFA (10.0 mL) and the solution stirred at RT under an argon atmosphere for 18 hours. After 18 hours, the solution was concentrated on a rotovap at RT. Toluene (25 mL) was added and the solution was concentrated again to remove TFA. The remaining oil was partitioned between water (25 mL) and dichloromethane (50 mL) and concentrated ammonium hydroxide solution (4 mL) was added until the aqueous fraction was neutral. The dichloromethane layer was separated and the aqueous portion was extracted with dichloromethane (25 mL). The combined dichloromethane extracts were dried over sodium sulfate, filtered, and concentrated. The reaction generated 3.75 g of crude free base that was a tan gel. The material was purified on a C18 reverse phase column (50 g, 17% carbon load) using a linear gradient of methanol/DI water (30% methanol to 100%) methanol. The purification was repeated 2 times in order to prepare 3-aminomethyl-docosa-7,10,13,16,19-pentaenoic acid (JIVA0040) (1.0 g, 31% yield) as a light yellow gel, and is further characterized by:

Analysis:

Appearance: light yellow gel

Chemical Formula: $C_{23}H_{37}NO_2$

Molecular Weight: 359.55

Chromatographic purity (HPLC): 96.2% (rt=12.277 min, 80-100% MeOH/H2O+0.1% TFA) over 10 min., hold 10 min., Synergi Max-RP, 5μ, 4.6×150 mm, 1.0 mL/min, 5 μL injection, 40° C., UV detection, 210 nm)

HRMS (ESI): Calculated for $C_{23}H_{38}NO_2$ (M+H)$^+$: 360.2897, found 360.2914.

$^1$H NMR (300 MHz, CD$_3$OD/TMS): δ 5.36 (m, 10 H), 2.97 (dd, 1 H, J=12.9, 3.6 Hz), 2.85-2.70 (m, 9 H), 2.45 (dd, 1H, J=15.6, 3.6), 2.28 (dd, 1H, J=15.6,8.1 Hz), 2.12-1.80 (m, 5H), 1.48-1.35 (m, 4H), 0.97(t, 3 H, J=7.5 Hz).

$^{13}$C NMR (300 MHz, CD$_3$OD/TMS): δ 180.5, 132.9, 130.8, 129.6, 129.4, 129.3, 129.2, 129.1, 129.0, 128.3, 45.6, 43.2, 35.7, 33.8, 28.3, 28.0, 26.7, 25.6, 21.6, 14.8.

EXAMPLE 3

Synthesis of ALA Analog of Isobutylgaba (JIVA0041):
3-Aminomethyl-eicosa-11,14,17-trienoic Acid Step 1): ALA olefin: Eicosa-2,11,14,17-tetraenoic acid tert-butyl ester

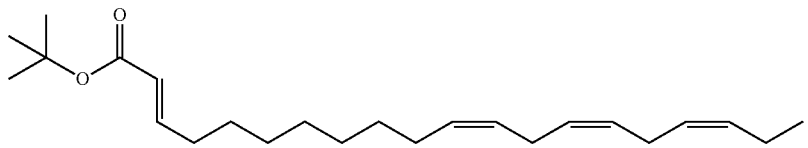 [SMILES: CC/C=C\C/C=C\C/C=C\CCCCCCC/C=C/C(=O)OC(C)(C)C]

Sodium hydride (60%, 1.0 g, 25 mmol) was stirred with anhydrous THF (70 mL) under an argon atmosphere. The flask was cooled in an ice bath, tert-butyl diethylphosphonoacetate (4.7 g, 18.4 mmol) was added drop-wise over 20 minutes and the mixtures stirred for an additional 30 minutes before the ALA-aldehyde (4.40 g, 15.4 mmol) in THF (20 mL) was added. The ice bath was removed and the reaction stirred for 3-4 hours at RT. Water (100 mL) was added and the product was extracted with heptanes (2×50 mL). The combined heptanes extracts were dried over sodium sulfate, filtered, and concentrated. The crude oil (10.2 g) was purified by flash column chromatography on silica gel (200 g), eluting with 5% ethyl acetate in heptanes. The experiment produced eicosa-2,11,14,17-tetraenoic acid tert-butyl ester (5.49 g, 99% yield) as a colorless oil, and is further characterized by:

$^1$H NMR (300 MHz, CDCl$_3$/TMS): δ 6.84 (dt, 1H, J=15.6, 7.2 Hz), 5.72 (d, 1H, J=15.6 Hz), 5.37 (m, 6 H), 2.81 (m, 4 H), 2.17-2.04 (m, 6H), 1.48 (s, 9H), 1.30 (m, 10H), 0.98 (t, 3H, J=7.8 Hz).

Step 2): ALA-nitromethyl analog: 3-Nitromethyl-eicosa-11,14,17-trienoic acid tert-butyl ester

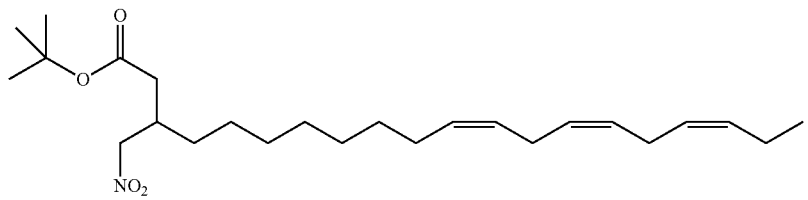 [SMILES: CC/C=C\C/C=C\C/C=C\CCCCCCCC(CC(=O)OC(C)(C)C)C[N+](=O)[O-]]

To a solution of eicosa-2,11,14,17-tetraenoic acid tert-butyl ester (5.49, 15.2 mmol) in nitromethane (50 mL) was added 1,1,3,3-tetramethylguanidine (2.0 g, 17.2 mmol). The resulting reaction mixture was allowed to stir at RT for 4 days. After 4 days, ethyl acetate (100 mL) was added and the base was extracted with 5% hydrochloroic acid solution (100 mL). The ethyl acetate extract was dried over sodium sulfate, filtered and concentrated. The crude oil was purified by silica gel (200 g) column chromatography (10% ethyl acetate/heptane). The experiment provided 3-nitromethyl-eicosa-11,14,17-trienoic acid tert-butyl ester (4.35 g, 79% yield), as a colorless oil, and is further characterized by:

$^1$H NMR (300 MHz, CDCl$_3$/TMS): δ 5.38 (m, 6 H), 4.45 (m, 2H), 2.81 (m, 4 H), 2.57 (m, 1H), 2.34 (m, 2H), 2.12-2.00 (m, 4H), 1.45 (s, 9H), 1.37-1.25 (m, 12H), 0.98 (t, 3H, J=7.7 Hz).

Steps 3,4): ALA-isobutylgaba analog (JIVA 0041): 3-Aminomethyl-eicosa-11,14,17-trienoic acid

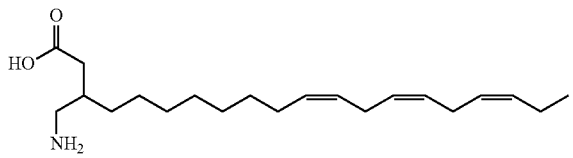 [SMILES: CC/C=C\C/C=C\C/C=C\CCCCCCCC(CN)CC(=O)O]

Zinc dust (4.5 g) was stirred with 10% hydrochloric acid (25 mL) for 4 to 5 minutes, filtered, and washed with DI water (2×50 mL) and methanol (2×50 mL). The activated zinc was added to methanol (50 mL) containing formic acid (4.5 mL, 97%) and 3-nitromethyl-eicosa-11,14,17-trienoic acid tert-butyl ester (4.35 g, 12.0 mmol). The mixture stirred for 3 hours at RT (flask was kept in a water bath to maintain RT). Toluene (40 mL) was added and the mixture was filtered through a pad of celite to remove the zinc. The methanol/toluene was concentrated on a rotovap. The remaining oil (5.1 g) was dissolved in dichloromethane (60 mL) and filtered to remove traces of zinc. The dichloromethane solution was added TFA (10.0 mL) and the solution stirred at RT under an argon atmosphere for 20 hours. After 20 hours, the solution was concentrated on a rotovap at RT. Toluene (25 mL) was added and the solution was concentrated again to remove TFA. The remaining oil was partitioned between water (25 mL) and dichloromethane (50 mL) and concentrated ammonium hydroxide solution (4 mL) was added until the aqueous fraction was neutral. The dichloromethane layer was separated and the aqueous portion was extracted with dichloromethane (25 mL). The combined dichloromethane extracts were dried over sodium sulfate, filtered, and concentrated. The reaction generated 3.40 g of crude free base that was a yellow gel. The material was purified on a C18 reverse phase column (50 g, 17% carbon load) using a linear gradient of methanol/DI water (30% methanol to 100%) methanol. The purification was repeated in order to prepare 3-aminomethyl-eicosa-11,14,17-trienoic acid (JIVA0041) (0.75 g, 19% yield) as a light yellow gel, and is further characterized by:

Analysis:
Appearance: light yellow gel
Chemical Formula: C$_{21}$H$_{37}$NO$_2$
Molecular Weight: 335.52
Chromatographic purity (HPLC): 95.9% (rt=12.38 min, 73-100% MeOH/H2O+0.1% TFA) over 10 min., hold 10 min., Altima C-18, 5μ, 4.6×250 mm, 1.0 mL/min, 5 μL injection, 40° C., UV detection, 210 nm)
HRMS (ESI): Calculated for C$_{21}$H$_{38}$NO$_2$ (M+H)$^+$: 336.2897, found 336.2906.

$^1$H NMR (300 MHz, CD$_3$OD/TMS): δ 5.36 (m, 6 H), 2.96 (dd, 1 H, J=12.9, 4.2 Hz), 2.95-2.70 (m, 6 H), 2.45 (dd, 1H, J=15.6, 3.6), 2.33-2.23 (m, 1H), 2.12-1.80 (m, 5H), 1.44-1.30 (m, 12H), 0.97 (t, 3 H, J=7.5 Hz).

$^{13}$C NMR (300 MHz, CD$_3$OD/TMS): δ 180.7, 132.9, 131.2, 129.4, 129.0, 128.4, 45.7, 43.3, 35.7, 34.1, 31.0, 30.7, 30.5, 28.4, 28.0, 26.7, 26.6, 21.6, 14.8.

Although the invention has been described with reference to its preferred embodiments, those of ordinary skill could prepare the target omegabalins by other common methodologies found in the chemical literature, e.g., Perumal Yogeeswari, et al., *Recent Patents on CNS Drug Discovery*, 2006, 1, 113-118.

Compounds of Formula (I) are preferably used as a pharmaceutically-acceptable formulation that has present one or more of pharmaceutically-acceptable adjuvants, binders, desiccants, diluents and excipients that are well known for such purpose. Such formulations are in the form of a solution for injection, ampoule, hard or soft gelatin capsule or tablet, or sustained release formulations. These formulations are used to treat persons for the treatment of neuropathic pain, fibromyalgia, epilepsy, anxiety, depression, insomnia, Alzheimer's disease and other neurological conditions.

Biology:
Muscimol is the principal psychoactive constituent of Amanita muscaria and related species of mushroom. Muscimol acts as a potent, selective agonist for the GABA$_A$ receptors and displays sedative-hypnotic and dissociative properties (WIKI). Affinity of compounds of Formula (I) and GABA (γ-aminobutyric acid) for GABA-A receptors labeled with [$^3$H] muscimol was determined for their ability to displace [$^3$H] muscimol.

Figure 2:
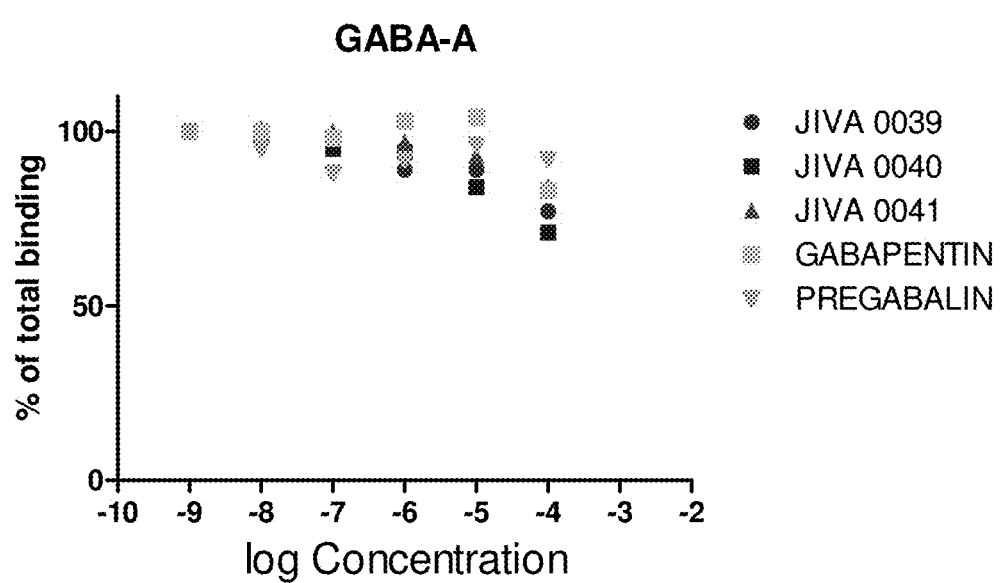
FIG. 2 graphically shows the affinity of compounds of Formula (I) made in Examples 1-3 and reference compounds pregabalin, and gabapentin for GABA-A receptors labeled with [$^3$H] muscimol.

It is shown by these tests that GABA inhibits binding with Ki=124.0+/−9.7 nM (mean+/−SEM) (FIG. 1), while low inhibition (max. 15%) was demonstrated by Formula (I)

compounds, including reference compounds pregabalin (S-isobutylgaba) and gabapentin (Table 1, FIG. 1 and 2). These tests were performed using the procedure described by Tomasz Plech et. al., *Studies on anticonvulsant activity of 4-alkyl*-1,2,4-*triazole*-3-*thiones and their effect on GABAergic system;* European J. of Medicinal Chem. 2014, 86, 690-699.

This is not surprising since pregabalin (S-isobutylgaba) itself is a weak agonist of GABA-A receptor. Pregabalin binds to the $\alpha_2\delta$ subunit (A2D)-containing voltage-gated calcium channels (VGCCs) and modulates calcium influx at the nerve terminals, which may account for its therapeutic effect on neuropathic pain, anxiety, and seizures (WIKI). Thus, to determine the neurological benefits of omegabalins versus pregabalin, further bioloy in animal models are planned; *Epilepsia,* 2004, 45 Suppl 6:13-8 *Pregabalin pharmacology and its relevance to clinical practice.* Ben-Menachem E[1].

In addition, omegabalins will be compared to vigabatrin which is unique in that it is a specific, irreversible inhibitor of the enzyme γ-aminobutyric acid α-oxoglutarate transaminase (GABA-T), which use leads to beneficial long lived elevated GABA levels in the brain.

TABLE 1

| COMPOUND | LOG OF MOLAR CONC. | % of [3H]-MUSCIMOL inhibition | SEM | LOG OF MOLAR CONC. | % of [3H]-MUSCIMOL inhibition | SEM |
|---|---|---|---|---|---|---|
| Example 1 (R = DHA) | −4 | 10% | 4% | −5 | 0% | 2% |
| Example 2 (R = EPA) | −4 | 15% | 4% | −5 | 10% | 3% |
| Example 3 (R = ALA) | −4 | 8% | 3% | −5 | 0% | 1% |
| GABA | −4 | 100% | 0% | −5 | 94% | 1% |
| Pregabalin | −4 | 12% | 1% | −5 | 0% | 0.5% |

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter.

What is claimed is:
1. Compounds of Formula (I):

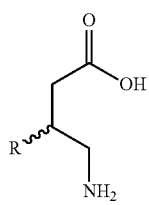

Formula (I)

wherein:
R is joined from the methylene moiety formed by reduction of the carboxylic acid of one of the following polyunsaturated fatty acids (PUFAs):
cis,cis,cis-7,10,13-hexadecatrienoic acid (HTA),
cis,cis,cis-9,12,15-octadecatrienoic acid (ALA),
cis,cis,cis-6,9,12,15-octadecatetraenoic acid (SDA),
cis,cis,cis-11,14,17-eicosatrienoic acid (ETE),
cis,cis,cis,cis-8,11,14,17-eicosatetraenoic acid (ETA);
cis,cis,cis,cis,cis-5,8,11,14,17-eicosapentanenoic acid (EPA),
cis,cis,cis,cis,cis-6,9,12,15,18-heneicosapentaenoic acid (HPA),
cis,cis,cis,cis,cis-7,10,13,16,19-docosapentaenoic acid (DPA),
cis,cis,cis,cis,cis-4,7,10,13,16,19-docosahexaenoic acid (DHA),
cis,cis,cis,cis,cis-9,12,15,18,21-tetracosapentaeonic acid (TPA) or
cis,cis,cis,cis,cis-6,9,12,15,18,21-tetracosahexaeonic acid (THA); and
the wavy bond depicts the creation of a new chiral carbon center forming two enantiomers of R and S configuration and mixtures thereof; or
pharmaceutically-acceptable salts of Formula (I).

2. The compound of claim 1 wherein R is joined from the methylene moiety formed by reduction of the carboxylic acid of EPA.

3. The compound of claim 1 wherein R is joined from the methylene moiety formed by reduction of the carboxylic acid of DHA.

4. The compound of claim 1 wherein R is joined from the methylene moiety formed by reduction of the carboxylic acid of ALA.

5. The compound of claim 1 wherein the compound is a RS mixture having chemical purity of ≥90% by weight.

6. The compound of claim 1, wherein the compound is either in an R or S configuration, wherein each isomer has a chemical purity of ≥90% by weight and enantiomeric purity of ≥90% by weight.

7. A pharmaceutical formulation having as its active ingredient one or more compounds of Formula (I) as defined in claim 1 including one or more pharmaceutically-acceptable adjuvants, binders, desiccants, diluents and excipients.

8. The pharmaceutical formulation of claim 7 in the form of a solution for injection, ampoule, hard or soft gelatin capsule, tablet, or as a sustained release formulation.

9. A method of treating a person needing such treatment for neuropathic pain, fibromyalgia, epilepsy, depression, insomnia by administrating to such person an effective amount of a pharmaceutical formulation of claim 7.

10. The method of claim 9, wherein the effective amount is from about 0.05 to about 5 g/day administered as 1-4 doses/day.

11. A method of treating a person needing such treatment for Alzheimer's disease by administrating to such person an effective amount of a pharmaceutical formulation of claim 7.

12. The method of claim 11, wherein the effective amount is from about 0.05 to about 5 g/day administered as 1-4 doses/day.

* * * * *